United States Patent
Queen

(10) Patent No.: US 7,456,139 B2
(45) Date of Patent: Nov. 25, 2008

(54) SOLVATED NONIONIC SURFACTANTS

(75) Inventor: Craig B. Queen, Middletown, DE (US)

(73) Assignee: Croda Uniqema, Inc., Chicago, IL (US)

( * ) Notice: Subject to any disclaimer, the term of this patent is extended or adjusted under 35 U.S.C. 154(b) by 0 days.

(21) Appl. No.: 10/840,418

(22) Filed: May 7, 2004

(65) Prior Publication Data

US 2005/0250669 A1    Nov. 10, 2005

(51) Int. Cl.
*C11D 1/72* (2006.01)
*C11D 3/32* (2006.01)
*C11D 3/20* (2006.01)

(52) U.S. Cl. .................. 510/119; 510/130; 510/137; 510/138; 510/421; 510/433; 510/501; 510/505

(58) Field of Classification Search ................. 510/124, 510/126, 127, 130, 137, 138, 502, 501, 505, 510/506; 424/70.11, 70.22, 70.31
See application file for complete search history.

(56) References Cited

U.S. PATENT DOCUMENTS

| | | | | |
|---|---|---|---|---|
| 4,544,495 A * | 10/1985 | Schmolka | .................. | 510/119 |
| 5,225,112 A | 7/1993 | Miyazawa et al. | | |
| 5,700,772 A * | 12/1997 | Isobe et al. | .................. | 510/421 |
| 5,723,111 A * | 3/1998 | Glover et al. | .............. | 424/70.1 |
| 6,339,057 B1 * | 1/2002 | Knox et al. | .................. | 510/421 |
| 6,440,907 B1 * | 8/2002 | Santora et al. | .............. | 510/121 |
| 6,495,498 B2 * | 12/2002 | Niemiec et al. | ............. | 510/122 |
| 6,514,918 B1 * | 2/2003 | Librizzi | ...................... | 510/124 |
| 6,750,192 B2 * | 6/2004 | Yamashita et al. | .......... | 510/421 |
| 6,770,607 B2 * | 8/2004 | Chen et al. | .................. | 510/158 |
| 2001/0027171 A1 * | 10/2001 | Sajac et al. | ................. | 510/124 |
| 2004/0235689 A1 * | 11/2004 | Sakai et al. | ................. | 510/119 |
| 2006/0036046 A1 * | 2/2006 | Sakai et al. | ................. | 525/474 |

FOREIGN PATENT DOCUMENTS

| | | |
|---|---|---|
| EP | 0125854 | 11/1984 |
| EP | 0743358 | 11/1996 |
| JP | 08337560 | 12/1996 |
| WO | 93/02169 | 2/1993 |
| WO | 2005/007242 | 1/2005 |

OTHER PUBLICATIONS

International Search Report for PCT/US2005/015271 dated Jul. 29, 2005.

* cited by examiner

*Primary Examiner*—Gregory R Del Cotto
(74) *Attorney, Agent, or Firm*—Jones Day

(57) ABSTRACT

A liquid and readily flowable composition includes (a) a room-temperature-solid solute comprising at least one nonionic surfactant, preferably having a hydrophile-lipophile balance from about 11.1 to about 18.8, (b) at least one fatty alkanolamide; and (c) water, if needed. The fatty alkanolamide, which is substantially liquid at room temperature, solvates the solid solute to form a homogeneous composition which is liquid and readily flowable at room temperature. The select classes of nonionic surfactants include polyalkylene oxide carboxylic acid esters, ethoxylated fatty alcohols, poloxamers, alkyl polysaccharides, or combinations thereof. Useful fatty alkanolamides include fatty diethanolamides.

19 Claims, No Drawings

SOLVATED NONIONIC SURFACTANTS

FIELD OF THE INVENTION

The present invention relates to solvating nonionic surfactants that are solid at room temperature with fatty alkanolamides and, at times, water. More specifically, the present invention relates to creating homogeneous solutions of these solid materials with fatty diethanolamides.

BACKGROUND OF THE INVENTION

Nonionic surfactants have been incorporated in a plethora of compositions because of the wide variety of utilities, such as adjuvancy, thickening, foaming, emulsification, dispersion, coupling (increasing the compatibility of oils), solubilization, detergency, suspension, spreading, wetting and gelling. Although nonionic surfactants have been available for more than fifty years, only a limited number have been provided in a readily flowable liquid form. Solid nonionic surfactants are typically heated to melt the solid into a flowable form for subsequent incorporation into various formulations.

Such heating, however, is not only expensive, but may also affect other ingredients of the resulting formulations. For example, certain surfactants have the ability to solubilize water insoluble materials, for example fragrances which are frequently only oil-soluble materials, into aqueous systems by reducing surface tension of the solution or by reducing interfacial surface tension between non-compatible substances to disperse the materials therein. Incorporation of fragrances into melted surfactants may often result in loss of the fragrances, as many of these substances are volatile oils.

Fatty alkanolamides have been used for many years in a variety of cosmetic, personal care, household and industrial formulations. Fatty alkanolamides are normally condensates of fatty acids with alkanolamines such as monoethanolamine, diethanolamine, and monoisopropanolamine. Fatty alkanolamides have been widely used in generally liquid systems such as liquid detergents and personal care products such as foam stabilizers, viscosity builders and the like, in metal working formulations as lubricants, viscosity control agents, corrosion inhibitors and in a variety of other applications.

As used in colloidal chemistry and as used in surfactant chemistry, solubilization is the dispersion or emulsion of an insoluble material into a liquid, such as water or a predominately aqueous system. Such a dispersion or emulsion, however, does not result in a true or intimate solution, i.e., a uniform mixture of a solute and a solvent at the molecular or ionic level. The solubilized mixture is finely dispersed to produce a visually clear emulsion having discrete particles present on the microscopic or micron level. In other words, certain surfactants, such as the above-described alkoxylated fatty alkanolamides, have been used to finely disperse or solubilize water-insoluble materials into aqueous systems, i.e., systems having predominant amounts of water. Such systems, however, remain heterogeneous, dual or multiple phases on a microscopic level.

Further, many nonionic surfactants are described as being soluble or slightly soluble in water, typically less than ten weight percent. Such commonly used terminology, however, does not refer to the ability of the surfactants to form true aqueous solutions, but refers to the limits for the amounts of the surfactants suitable for aqueous dispersion or emulsification.

While various dispersions of fatty alkanolamides and surfactant systems or formulations containing fatty alkanolamides have been described, solvation of nonionic surfactants compositions that are solid at room temperature has remained elusive. Consequently, there is a need to solvate nonionic surfactants that are substantially solid at room temperature to provide a homogeneous liquid which is stable at room temperature. Desirably, such solvations will provide the known attributes of the solid nonionic surfactants, while providing the convenience of being liquid-form deliverable.

SUMMARY OF THE INVENTION

The present invention relates to the solvation of certain nonionic surfactants which are solid at ambient, room temperature (about 25° C.). Desirably, the solvation does not adversely affect the attribute for which the nonionic surfactant is normally added to a composition or a formulation. In some cases, the solvation results in a synergistic affect where the solvated composition offers enhanced performance as compared to the use of an unsolvated nonionic surfactant.

More specifically, the present invention relates to a homogeneous liquid composition of nonionic surfactants, at least one fatty alkanolamide and, at times, water. In a preferred embodiment fatty diethanolamides are employed. Not all nonionic surfactants, however, may be effectively solvated by the fatty alkanolamides. Those surfactants of classes described herein preferably have a hydrophile-lipophile balance (HLB) about 11.1 to about 18.8. Nonionic surfactants having an HLB less than about 11.1 or greater than about 18.8 may not be completely solvated with the fatty alkanolamides used in the present invention.

Useful fatty diethanolamides include lauric diethanolamide and coconut oil fatty diethanolamide, and combinations thereof.

DETAILED DESCRIPTION OF THE INVENTION

A large number of applications are contemplated by the present invention. Among the many applications in which the solvated compositions of the present invention may be incorporated include, without limitation, skin care products such as soap, liquid hand cleansers, body washes, facial washes, lotions, moisturizers, sun screens, and make-up; hair care products such as shampoos, conditioners, hair dyes and colorants and hair gels; industrial cleaners; household cleaners; laundry detergents; as well as pre-moistened towels such as baby wipes and geriatric wipes; agricultural products including pesticides; paints; textiles; metal cleaning products; metal working products; and lubricants.

As used herein to describe the present invention, and as used in general chemistry, the term salvation and its variants relate to the ability of a material (i.e., a solvent) to form a homogeneous liquid solution with another substance (i.e., a solute) through molecular interactions, but excluding substantial molecular dissociation of the solute, such as the case with sodium chloride being dissolved by water. In such a homogeneous solution the solute is dissolved by the solvent. In contrast, as described above, solubilization relates to the ability of a material (a solubilizer) to aid in the dispersion of two noncompatible, for example, immiscible, substances. Often the solubilizer reduces the interfacial surface tension between the immiscible substances to permit dispersion therebetween. Such a dispersion does not result in a homogeneous liquid solution, but merely results in a heterogeneous, often times finely dispersed micro-emulsion mixture. Thus, as used herein, the degree of homogeneity for solvated compositions exceeds the degree of homogeneity present in solubilized compositions. As used herein, a homogeneous composition refers to a uniform composition or true solution that does not separate into individual constituents over time at about room temperature, even when subjected to freezing and subsequent thawing.

Useful solvents with the practice of the present invention include liquid fatty alkanolamides, preferably fatty diethanolamides, and, at times, water. Solutes which may be solvated by such solvents include certain nonionic surfactants which are solid at room temperature. The nonionic surfactants that are solvated with the fatty alkanolamides include those classes of nonionic surfactants described below, preferably having a hydrophile-lipophile balance (HLB) about 11.1 to about 18.8.

The HLB is an indication of the weight amount of the hydrophilic portion of the nonionic surfactant. HLB values for most polyol fatty acid esters can be calculated with the formula HLB=20*(1−S/A), where S is the saponification number of the ester and A is the acid number of the recovered acid. Where the hydrophilic portion consists of ethylene oxide, the HLB value may be calculated with the formula HLB=E/5, where E is the weigh percent of oxyethylene content.

The solutes of the present invention are those that are solid at room temperature and selected from nonionic surfactants preferably having an HLB from about 11.1 to about 18.8, and selected from the following classes:

(1) polyalkylene oxide carboxylic acid esters having from about 8 to about 30 carbon atoms and having a polyethylene oxide moiety corresponding to the formula —$(OCH_2CH_2)_n$, where n is from about 5 to about 200, and further where both mono- and di-esters are included, and preferably having from about 16 to about 18 carbon atoms and where n is from about 8 to about 150;

(2) ethoxylated fatty alcohols having an ethylene oxide moiety corresponding to the formula —$(OCH_2\ CH_2)_m$, wherein m is from about 5 to about 150, preferably from about 6 to about 31, and more preferably from about 7 to about 21 moles of ethoxylation, and having a fatty alcohol moiety having from about 6 to about 30 carbon atoms, preferably from about 8 to about 22 carbon atoms, and more preferably from about 10 to about 19 carbon atoms, where these fatty alcohols can be straight or branched chain alcohols and can be saturated or unsaturated, and where nonlimiting examples of suitable ethoxylated fatty alcohols include oleth-10 through oleth-20, which are ethylene glycol ethers of oleth alcohol, wherein the numeric designation indicates the number of ethylene oxide moieties present, the steareth series of compounds such as steareth-10 through steareth-21, which are ethylene glycol ethers of steareth alcohol, wherein the numeric designation indicates the number of ethylene oxide moieties present, and other fatty alcohols may include lauryl alcohol and isocetyl alcohol;

(3) poloxamers, which are ethylene oxide and propylene oxide block copolymers, having from about 15 to about 100 moles of ethylene oxide, preferably, about 60 to about 70 moles, and having about 15 to about 70 moles of propylene oxide, preferably, about 20 to about 30 moles;

(4) alkyl polysaccharide (APS) surfactants (e.g. alkyl polyglycosides) having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy); and (5) combinations thereof.

Preferred solutes are polyalkylene oxide carboxylic acid esters, ethoxylated fatty alcohols, and combinations thereof.

The amount of solute present in the homogeneous compositions of the present invention may vary from low concentrations, for example about 10 weight percent or less, to high concentrations, for example about 80 weight percent or greater, where the weight percents are on a total composition basis. The amount of the above-described nonionic surfactants that may be solvated depends upon several factors, including the HLB of the nonionic surfactant to be solvated. Other factors may include the particular solvent, including water, if present. At terminal ends of the preferred HLB range, i.e., about 11.1 and about 18.8, about 10 weight percent nonionic surfactant may suitably be solvated. Solutions having less than 10 weight percent nonionic surfactant may also be formed, but these more dilute solutions are not preferred as functionality of the surfactant may be diluted. Higher amounts of nonionic surfactants may be solvated at HLB values between the 11.1 and 18.8 values. For example, about 80 weight percent or greater of nonionic surfactants having an HLB from about 15 to about 17 may be solvated. Accordingly, the true solutions of room-temperature-solid nonionic surfactants having HLB values between about 11.1 and about 18.8 values may be formed having from about 10 weight percent to about 80 weight percent nonionic surfactant on a total composition basis, preferably from about 20 weight percent to about 70 weight percent, and more generally from about 20 weight percent to about 65 weight percent.

Solvation levels for certain nonionic surfactants with fatty alkanolamides vary with HLB of the nonionic surfactants, and, at times, water. Numerous testing was done at less than the maximum solvation limits to confirm the homogeneity of the resulting compositions at varying concentrations of solute and solvent. Nonionic surfactants having a HLB of less than about 11.1 tend to form cloudy or hazy mixtures with possible phase separation. Nonionic surfactants having a HLB of greater than about 18.8 tend to be cloudy or hazy mixtures with possible phase separation and possible solidification.

The above-described solvation levels may also suitably be used for blends or combinations of nonionic surfactants, whereby the resulting HLB of the nonionic surfactant blend is preferably within from about 11.1 to about 18.8. Thus, a blend of a nonionic surfactant having a HLB from about 11.1 to about 18.8 and another nonionic surfactant, which may or may not have a HLB from about 11.1 to about 18.8, may suitably be solvated, provided that the combined HLB is preferably from about 11.1 to about 18.8. Preferably, only minor amounts of nonionic surfactants outside of the HLB range of about 11.1 to about 18.8 are included in surfactant blends to be solvated.

Solvation levels for the nonionic surfactants also depend upon the amount of solvent used. Fatty alkanolamides in the amounts from about 10 weight percent to about 80 weight percent on a total combination basis may be present in the solvated compositions of the present invention, preferably from about 20 weight percent to about 70 weight percent, and more preferably from about 20 weight percent to about 65 weight percent. Some water may be required for solvation of the nonionic surfactants with fatty alkanolamides to form homogeneous liquid solutions. Generally, at least 5 weight percent water is used for forming homogeneous liquid compositions with nonionic surfactants. The homogeneous liquid compositions may suitably contain from about 5 weight percent to about 35 weight percent water on a total composition basis, preferably from about 10 to about 30 weight percent water, more preferably from about 20 to about 30 weight percent water.

The fatty moiety of the fatty alkanolamide is preferably a branched or straight chain, alkyl or alkenyl group containing 3 to 21 carbon atoms, more preferably containing 8 to 18 carbon atoms, or a combination thereof. Straight chain alkyl groups are preferred. The fatty alkanolamides may be fatty ethanolamides or fatty isopropanolamides, but fatty ethanolamides, particularly fatty diethanolamides are preferred.

Suitable preferred fatty diethanolamides include lauric diethanolamide, capric diethanolamide, caprylic diethanolamide, caprylic/capric diethanolamide, decanoic diethanolamide, myristic diethanolamide, palmitic diethanolamide, stearic diethanolamide, isostearic diethanolamide, oleic diethanolamide, linoleic diethanolamide, octyldecanoic diethanolamide, 2-heptylundecanoic diethanolamide, coconut oil fatty diethanolamide, beef tallow fatty diethanolamide, soy oil fatty diethanolamide and palm kernel oil fatty diethanolamide. Of these lauric and coconut oil fatty diethanolamides are preferred.

A method for solvating a room-temperature-solid solute according to the present invention comprises the steps of (a) providing a room-temperature-solid solute of at least one nonionic surfactant, preferably having a hydrophile-lipophile balance from about 11.1 to about 18.8, (b) selecting at least one fatty alkanolamide which is liquid at room temperature, (c) combining the solute, optionally the water, and the fatty alkanolamide; (d) heating the mixture to a temperature greater than the pour point of the solute to liquefy the solid; and (e) maintaining temperature of the mixture and stirring until a homogeneous liquid composition is achieved. The composition may be cooled to room temperature to form a room-temperature, homogenous liquid composition. The present invention, however, is not limited to heating the combined mixture for liquefaction of the solute. For example, any of the constituents may be heated, individually or in combination, to provide sufficient enthalpy to melt the solid solute and to keep the resultant mixture in liquid form during mixing. The heating may be done prior, during or after combining the different constituents.

The solvation techniques of the present invention provide a liquid and readily flowable composition comprising (a) a room-temperature-solid solute of at least one a nonionic surfactant, such as polyalkylene oxide carboxylic acid esters, ethoxylated fatty alcohols, poloxamers, alkyl polysaccharides, and combinations thereof, preferably having a hydrophile-lipophile balance from about 11.1 to about 18.8, and (b) at least one fatty alkanolamide composition; and optionally (c) water, when needed.

When the solute comprises a polyalkylene oxide carboxylic acid diester, preferably polyoxyethylene (150) distearate, the use of a solvent comprising a fatty alkanolamide, preferably a fatty diethanolamide, and water results in a synergistic thickening effect. By synergistic is meant the resultant thickening is greater than the thickening caused by the solute alone or the solvent alone. Such synergistic thickening is useful in cleansing formulations, for example, but not limited to, shampoos. The solvated composition according to the present invention has surprisingly enhanced thickening over the contributions of its individual constituents. The fatty alkanolamide, suitably fatty diethanolamide, is preferably present in the amounts from about 5 weight percent to about 50 weight percent on a total combination basis in the solvated compositions of the present invention, preferably from about 10 weight percent to about 35 weight percent, and more preferably from about 15 weight percent to about 25 weight percent. The polyalkylene oxide carboxylic acid diester is preferably present in the amounts from about 20 weight percent to about 70 weight percent on a total combination basis, preferably from about 30 weight percent to about 60 weight percent, and more preferably from about 45 weight percent to about 55 weight percent. The homogeneous liquid compositions suitably contain from about 5 weight percent to about 50 weight percent water on a total composition basis, preferably from about 15 to about 40 weight percent water, more preferably from about 25 to about 30 weight percent water. A particularly surprising feature is that relatively high concentrations of polyalkylene oxide carboxylic acid diester can be solvated using relatively low concentrations of fatty alkanolamide.

In one aspect of the present invention, a shampoo is provided which comprises, i.e. is formed from a liquid and readily flowable composition defined herein, and additionally comprises an anionic surfactant; and optionally one or more of a betaine, a non-ionic surfactant, an amphoteric surfactant, and a cationic surfactant.

In a further aspect a baby shampoo is provided. The baby shampoo comprises (i) a room-temperature liquid and solvated thickening composition comprising (a) a solvent comprising at least one fatty alkanolamide; preferably a fatty diethanolamide, (b) a solute comprising a room-temperature-solid nonionic surfactant comprising polyalkylene oxide carboxylic acid diesters having a polyethylene oxide moiety corresponding to the formula of $(OCH_2CH_2)_n$, where n is from about 5 to about 200, and having a carboxylic acid moiety from about 8 to about 30 carbon atoms, preferably having a hydrophile-lipophile balance from about 11.1 to about 18.8; and (c) water; (ii) an anionic surfactant; (iii) a betaine; (iv) a nonionic surfactant; and (v) optionally, an amphoteric surfactant. Preferably, the anionic surfactant is present from about 2 to about 5 weight percent on a total shampoo basis; the betaine is present from about 3 to about 6 weight percent on a total shampoo basis; the nonionic surfactant is present from about 6 to about 10 weight percent on a total shampoo basis; and the amphoteric surfactant is present from about 0 to about 5 weight percent on a total shampoo basis. Non-limiting examples of anionic surfactants useful for baby shampoos include sodium trideceth sulfate. Non-limiting examples of betaines useful for baby shampoos include cocamidopropyl betaine. Non-limiting examples of nonionic surfactants useful for baby shampoos include PEG sorbitan laurate. Non-limiting examples of amphoteric surfactants useful for baby shampoos includes sodium laureth sulfate.

In another aspect of the present invention an adult shampoo is provided. The adult shampoo comprises (i) a room-temperature liquid and solvated thickening composition comprising: (a) a solvent comprising at least one fatty alkanolamide; preferably a fatty diethanolamide, (b) a solute comprising a room-temperature-solid nonionic surfactant comprising polyalkylene oxide carboxylic acid diesters having a polyethylene oxide moiety corresponding to the formula of $(-OCH_2CH_2)_n$, where n is from about 5 to about 200, and having a carboxylic acid moiety from about 8 to about 30 carbon atoms, preferably having a hydrophile-lipophile balance from about 11.1 to about 18.8; and (c) water; (ii) anionic surfactant; (iii) betaine; (iv) nonionic surfactant; and (v) optionally, cationic surfactant. Preferably, the anionic surfactant is present from about 6 to about 15 weight percent on a total shampoo basis; the betaine is present from about 2 to about 6 weight percent on a total shampoo basis; the nonionic surfactant is present from about 1 to about 4 weight percent on a total shampoo basis; and the cationic surfactant is present from about 0 to about 1 weight percent on a total shampoo basis. Non-limiting examples of anionic surfactants useful for adult shampoos include sodium laureth sulfate, sodium lauryl sulfate, ammonium laureth sulfate, ammonium lauryl sulfate, alpha-olefin sulfonate, and combinations thereof. Non-limiting examples of betaine useful for adult shampoos include cocamidopropyl betaine. Non-limiting examples of nonionic surfactants useful for adult shampoos include cocamide MEA, lauramide DEA, PPG-2 hydroxyethyl coco/isostearamide, and combinations thereof. Non limiting examples of cationic surfactants useful for adult shampoos includes Polyquat-10 or behentrimonium chloride.

In another aspect of the present invention an industrial cleaning composition, preferably a laundry detergent is provided. The industrial cleaning composition comprises:
(i) a liquid and readily flowable composition comprising:
a) a room-temperature-solid solute comprising at least one nonionic surfactant,
b) at least one fatty alkanolamide; and
c) optionally water;
wherein the fatty alkanolamide acts as a solvent to solvate the solid solute to form a homogeneous composition which is liquid and readily flowable at room temperature; and
(ii) at least one surfactant selected from the group consisting of an anionic surfactant; a non-ionic surfactant, an amphoteric surfactant, and a cationic surfactant.

The features and advantages of the present invention are more fully shown by the following examples which are provided for purposes of illustration, and are not to be construed as limiting the invention in any way.

EXAMPLES

Examples 1 through 6 demonstrate the ability of the fatty alkanolamides to solvate selected room-temperature-solid materials. The selected room-temperature-solid materials were combined with the fatty alkanolamide water at various concentrations. The solid materials in Examples 1-6 were added to the fatty alkanolamides and heated to a temperature of 50° C. or to a temperature slightly greater than their melting or pour point when it exceeded 50° C. to provide a liquefied material. The material was stirred in a vessel with a mixing blade while maintaining temperature until homogeneous. Water was separately heated to a temperature of about 50° C. The heated water was added to the blend with moderate stirring. The resulting mixtures were cooled to room temperature.

Example 1

Polyoxyethylene (20) isohexadecyl ether (Arlasolve 200, available from Uniqema) which has a HLB of about 15.7, is a solid at room temperature (34° C. pour point, was combined with lauric diethanolamide (Monamid 716, available from Uniqema) or coconut oil fatty diethanolamide (Monamid 705, available from Uniqema), and water at the proportions described below and according to the procedures described above to form a solvated, clear and homogeneous composition. The results are shown below in Table 1.

TABLE 1

| Polyoxyethylene (20) isohexadecyl ether, Wt. % | Lauric or Coconut oil fatty diethanolamide, Wt. % | Water, Wt. % | Appearance at 20° C. |
|---|---|---|---|
| 20 | 65 | 15 | clear, soluble, pourable |

Example 2

The procedure of Example 1 was repeated except that polyoxyethylene (10) stearyl ether (Brij 76, available from Uniqema) which has a HLB of about 12.4, is a solid at room temperature (38° C. pour point) was used. The results are shown below in Table 2.

TABLE 2

| Polyoxyethylene (10) stearyl ether, Wt. % | Lauric or Coconut oil fatty diethanolamide, Wt. % | Water, Wt. % | Appearance at 20° C. |
|---|---|---|---|
| 20 | 65 | 15 | clear, soluble, pourable |

Example 3

The procedure of Example 1 was repeated except that polyoxyethylene (20) stearyl ether (Brij 78, available from Uniqema) which has a HLB of about 15.3, is a solid at room temperature (38° C. pour point) was used. The results are shown below in Table 3.

TABLE 3

| Polyoxyethylene (20) stearyl ether, Wt. % | Lauric or Coconut oil fatty diethanolamide, Wt. % | Water, Wt. % | Appearance at 20° C. |
|---|---|---|---|
| 20 | 65 | 15 | clear, soluble, pourable |

Example 4

The procedure of Example 1 was repeated except that polyoxyethylene (21) stearyl ether (Brij 721, available from Uniqema) which has a HLB of about 15.5, is a solid at room temperature (45° C. pour point) was used. The results are shown below in Table 4.

TABLE 4

| Polyoxyethylene (21) stearyl ether, Wt. % | Lauric or Coconut oil fatty diethanolamide, Wt. % | Water, Wt. % | Appearance at 20° C. |
|---|---|---|---|
| 20 | 65 | 15 | clear, soluble, pourable |

Example 5

The procedure of Example 1 was repeated except that polyoxyethylene (100) stearate (Myrj 59, available from Uniqema) which has a HLB of about 18.8, is a solid at room temperature (46° C. pour point was) used. The results are shown below in Table 5.

TABLE 5

| Polyoxyethylene (100) stearate, Wt. % | Lauric or Coconut oil fatty diethanolamide, Wt. % | Water, Wt. % | Appearance at 20° C. |
|---|---|---|---|
| 20 | 65 | 15 | clear, soluble, pourable |

Example 6

The procedure of Example 1 was repeated except that polyoxyethylene (150) distearate (Estol 3734, available from Uniqema) which has a HLB of about 18.4, is a solid at room temperature (55° C. pour point) was used. The results are shown below in Table 6.

TABLE 6

| Polyoxyethylene (150) distearate, Wt. % | Lauric or Coconut oil fatty diethanolamide, Wt. % | Water, Wt. % | Appearance at 20° C. |
|---|---|---|---|
| 50 | 20 | 30 | clear, soluble, pourable |

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A homogenous liquid and readily flowable at room temperature composition obtained by solvating components consisting of:
   a) about 10 wt. % to about 80 wt. % based on the total composition of a room-temperature-solid solute, wherein said solute is at least one polyalkylene oxide carboxylic acid ester,
   b) about 20 wt. % to about 80 wt. % based on the total composition of one or more fatty alkanolamides selected from the group consisting of: lauric diethanolamide, capric diethanolamide, caprylic/capric diethanolamide, caprylic diethanolamide, decanoic diethanolamide, myristic diethanolamide, palmitic diethanolamide, stearic diethanolamide, isostearic diethanolamide, oleic diethanolamide, linoleic diethanolamide, octyldecanoic diethanolamide, 2-heptylundecanoic diethanolamide, coconut oil fatty diethanolamide, beef tallow fatty diethanolamide, soy oil fatty diethanolamide, and palm kernel oil diethanolamide; and
   c) optionally water.

2. The composition of claim 1 wherein the polyalkylene oxide carboxylic acid ester has a hydrophile-lipophile balance from about 11.1 to about 18.8.

3. The composition of claim 1 wherein the polyalkylene oxide carboxylic acid ester is selected from the group consisting of
   polyalkylene oxide carboxylic acid monoesters, polyalkylene oxide carboxylic acid diesters, and combinations thereof, wherein the polyalkylene oxide carboxylic acid ester has a polyethylene oxide moiety corresponding to the formula of $-(OCH_2CH_2)_n-$, where n is from about 5 to about 200, and has a carboxylic acid moiety from about 8 to about 30 carbon atoms.

4. The composition of claim 1 wherein the polyalkylene oxide carboxylic acid ester has a polyethylene oxide moiety corresponding to the formula of $-(OCH_2CH_2)_n-$, where n is from about 5 to about 200, and has a carboxylic acid moiety from about 8 to about 30 carbon atoms.

5. The composition of claim 1 wherein the addition of the composition into a cleansing formulation increases viscosity of the cleansing formulation to a greater viscosity than for similar weight additions of unsolvated polyalkylene oxide carboxylic acid esters into the cleansing formulation.

6. The composition of claim 1 wherein the polyalkylene oxide carboxylic acid ester is selected from the group consisting of
   polyalkylene oxide carboxylic acid monoesters, polyalkylene oxide carboxylic acid diesters, and combinations thereof, wherein the polyalkylene oxide carboxylic acid esters have a polyethylene oxide moiety corresponding to the formula of $-(OCH_2CH_2)_n-$, where n is from about 8 to about 150, and have a carboxylic acid moiety from about 16 to about 18 carbon atoms.

7. A method of thickening a cleansing formulation comprising:
   adding to the cleansing formulation a solvated liquid premixture composition that consists of:
   (a) about 15 wt. % to about 50 wt. % based on the total premixture composition of a solvent, wherein said solvent is at least one fatty alkanolamide selected from the group consisting of: lauric diethanolamide, capric diethanolamide, caprylic/capric diethanolamide, caprylic diethanolamide, decanoic diethanolamide, myristic diethanolamide, palmitic diethanolamide, stearic diethanolamide, isostearic diethanolamide, oleic diethanolamide, linoleic diethanolamide, octyldecanoic diethanolamide, 2-heptylundecanoic diethanolamide, coconut oil fatty diethanolamide, beef tallow fatty diethanolamide, soy oil fatty diethanolamide, and palm kernel oil diethanolamide; and;
   (b) about 20 wt. % to about 70 wt. % based on the total premixture composition of a room-temperature-solid solute, wherein said solute is at least one polyalkylene oxide carboxylic acid diester having a polyethylene oxide moiety corresponding to the formula of $-(OCH2CH2)_n-$, where n is from about 5 to about 200, and having a carboxylic acid moiety from about 8 to about 30 carbon; and
   (c) about 5 wt. % to about 50 wt. % water;
   wherein the solvated liquid premixture composition is a homogeneous liquid at room temperature.

8. The method of claim 7 wherein the step of adding the solvated liquid premixture composition is performed at room temperature.

9. The method of claim 7 wherein the addition of the solvated liquid premixture composition increases viscosity of the cleansing formulation to a greater extent than by the addition of similar weight amounts of a similar polyalkylene oxide carboxylic acid diester.

10. The method of claim 7 wherein the cleansing formulation is a shampoo.

11. The liquid and readily flowable composition of claim 1 wherein said at least one fatty alkanolamide is present in an amount from about 20 wt. % to about 70 wt. %.

12. A homogenous liquid and readily flowable at room temperature composition obtained by solvating components consisting of:
   a) about 10 wt. % to about 80 wt. % based on the total composition of a room-temperature-solid solute, wherein said solute is at least one polyalkylene oxide carboxylic acid ester,
   b) about 20 wt. % to about 80 wt. % based on the total composition of one or more fatty alkanolamides selected from the group consisting of: lauric diethanolamide, capric diethanolamide, caprylic/capric diethanolamide, caprylic diethanolamide, decanoic diethanolamide, myristic diethanolamide, palmitic diethanolamide, stearic diethanolamide, isostearic diethanolamide, oleic diethanolamide, linoleic diethanolamide, octyldecanoic diethanolamide, 2-heptylundecanoic diethanolamide, coconut oil fatty diethanolamide, beef tallow fatty diethanolamide, soy oil fatty diethanolamide, and palm kernel oil diethanolamide; and c) about 5 wt. % to about 35 wt % based on the total composition of water.

13. A homogenous liquid and readily flowable at room temperature composition obtained by solvating components consisting of:

(a) about 15 wt. % to about 50 wt % based on the total composition of a solvent, wherein said solvent is at least one fatty alkanolamide selected from the group consisting of: lauric diethanolamide, capric diethanolamide, caprylic/capric diethanolamide, caprylic diethanolamide, decanoic diethanolamide, myristic diethanolamide, palmitic diethanolamide, stearic diethanolamide, isostearic diethanolamide, oleic diethanolamide, linoleic diethanolamide, octyldecanoic diethanolamide, 2-heptylundecanoic diethanolamide, coconut oil fatty diethanolamide, beef tallow fatty diethanolamide, soy oil fatty diethanolamide, and palm kernel oil diethanolamide; and;

(b) about 20 wt. % to about 70 wt. % based on the total composition of a room-temperature-solid solute, wherein said solute is at least one polyalkylene oxide carboxylic acid ester; and (c) about 5 wt. % to about 50 wt. % water;

wherein the solvated thickening composition is a homogeneous liquid at room temperature.

14. The method of claim 7, wherein the room-temperature-solid solute is at least polyoxyethylene (150) distearate.

15. The method of claim 7, wherein at least one of the fatty alkanolamides is lauric or coconut oil diethanolamide.

16. The composition of claim 12, wherein the room-temperature-solid solute is at least polyoxyethylene (150) distearate.

17. The composition of claim 12, wherein one or more of the fatty alkanolamides is lauric or coconut oil diethanolamide.

18. The composition of claim 13, wherein the room-temperature-solid solute is at least polyoxyethylene (150) distearate.

19. The composition of claim 13, wherein at least one of the fatty alkanolamides is lauric or coconut oil diethanolamide.

* * * * *